United States Patent [19]

Dany et al.

[11] 4,032,498

[45] June 28, 1977

[54] FLAME-RETARDANT PLASTICIZERS FOR POLYVINYL CHLORIDE

[75] Inventors: Franz-Josef Dany, Erftstadt; Joachim Wortmann, Turnich; Peter Münch; Hartfrid Vollmer, both of Erftstadt, all of Germany

[73] Assignee: Hoechst Aktiengesellschaft, Frankfurt am Main, Germany

[22] Filed: Oct. 21, 1975

[21] Appl. No.: 624,545

[30] Foreign Application Priority Data

Oct. 24, 1974 Germany .......................... 2450949

[52] U.S. Cl. .............. 260/30.6 R; 260/32 XA; 260/DIG. 24; 260/928; 260/929; 260/930
[51] Int. Cl.² ........................................ C08K 5/52
[58] Field of Search ............. 260/30.6 R, 928, 929, 260/930

[56] References Cited

UNITED STATES PATENTS 3,968,187 7/1976 Morgan et al. .................... 260/928

*Primary Examiner*—Stanford M. Levin
*Attorney, Agent, or Firm*—Connolly and Hutz

[57] ABSTRACT

Flame-retardant PVC-plasticizers of the general formula (I)

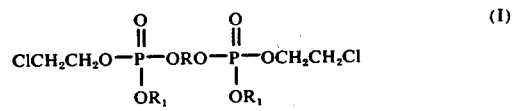

in which R stands for an alkylene radical or a halogen-substituted alkylene radical having from 2 to 6 carbon atoms, a $-CH_2CH_2-O-CH_2CH_2-$ radical, a phenylene or an alkyl or halogenoalkyl-substituted diphenylenemethane radical and $R_1$ stands for a branched or unbranched alkyl radical having from 6 to 18 carbon atoms.

18 Claims, No Drawings

FLAME-RETARDANT PLASTICIZERS FOR POLYVINYL CHLORIDE

Unmodified polyvinyl chloride, which has considerable chlorine in the molecule, has by nature very good flame-retardant properties. Polyvinyl chloride is, however, rapidly deprived of its natural flame-retardant properties on being elasticized with the use of a plasticizer which contains neither a halogen or phosphorus atom in the molecule. Known plasticizers include, e.g., phthalates, sebacates, adipates or epoxides. They are used if no particularly high demands are made as to the flame-resistance of polyvinyl chloride.

The initial flame-retardant properties of unmodified polyvinyl chloride, briefly termed PVC hereinafter, remain unaffected if a phosphorus-containing plasticizer is incorporated therewith. Customary phosphorus-containing plasticizers include, e.g., triaryl, trialkyl and aralkyl phosphates, and more especially tricresyl phosphate, triphenyl phosphate, diphenylcresyl phosphate or tridodecyl phosphate.

It is also known that PVC can be rendered flameproof by means of chlorine-containing paraffins.

Good flame-retardant plasticizers for PVC are expected firstly to impart to PVC satisfactory flame-retardant properties and secondly to have properties as advantageous as those of customary plasticizers, which make it possible for the plasticizers to permanently remain in PVC and substantially not to migrate therefrom, so that the PVC/plasticizer-blend in fact remains difficultly inflammable and flexible.

A further important property demanded of a plasticizer is its ability of imparting good low temperature flexibility to the PVC blend and accordingly freeze-resistance to plasticized PVC.

Known flame-retardant PVC-plasticizers do, however, not fully comply with these requirements for more or less great lack of one or more of the above properties.

It is accordingly an object of the present invention to provide flame-retardant plasticizers for PVC, which may be used in admixture with known plasticizers being free from, or having not fully satisfactory, flame-retardant properties, impart optimum flame-retardant effects to plasticized PVC, and do not adversely affect or otherwise influence the plasticizing efficiency of such known plasticizers.

We have now unexpectedly found that compounds of the following general formula (I) satisfy the requirements demanded of a flame-retardant plasticizer for PVC.

The flame-retardant PVC-plasticizers of the present invention have the following general formula (I)

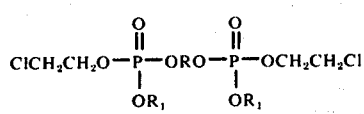

(1)

in which R stands for an alkylene radical having from 2 to 6 carbon atoms and being halogen-substituted, if desired, a —CH$_2$CH$_2$—O—CH$_2$CH$_2$—radical, a phenylene or an alkyl or halogeno-alkyl-substituted diphenylenemethane radical and R$_1$ stands for a branched or unbranched alkyl radical having from 6 to 18 carbon atoms.

In those cases in which the substituent R in formula (1) stands for a halogenoalkyl-substituted diphenylenemethane radical, it is possible for chlorine or bromine to be used as the halogen. Preferably, however, the substituent R stands for an ethylene, hexamethylene or diethyleneglycol radical or for one of the following two radicals

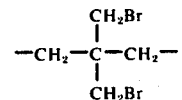 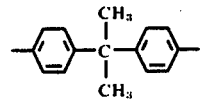

The invention comprises more specifically the following flame-retardant plasticizers having the following formulae:

a) 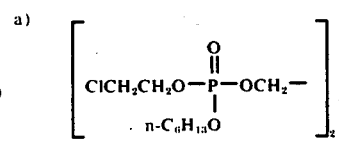

b) 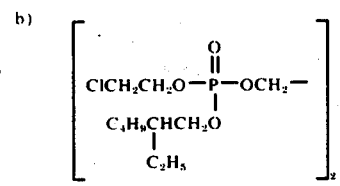

c) 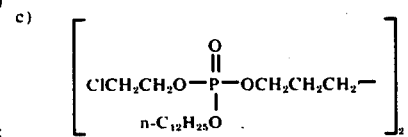

d) 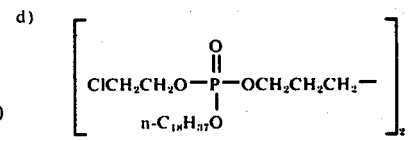

e) 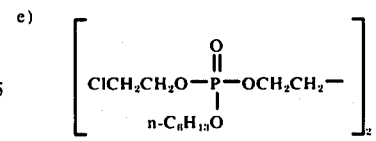

f) 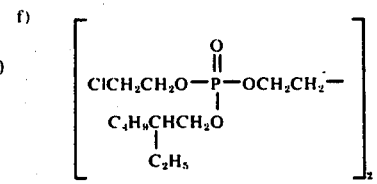

g) 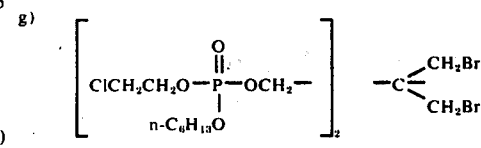

h) 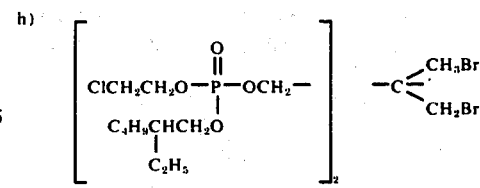

-continued i)
$$\left[ClCH_2CH_2O-\underset{\underset{n-C_6H_{13}O}{|}}{\overset{\overset{O}{\|}}{P}}-O-\underset{}{\underset{}{\bigcirc}}-\right]_2 -C\overset{CH_3}{\underset{CH_3}{\diagdown}}$$

k)
$$\left[ClCH_2CH_2O-\underset{\underset{\underset{C_2H_5}{|}}{C_4H_9CHCH_2O}}{\overset{\overset{O}{\|}}{P}}-O-\underset{}{\underset{}{\bigcirc}}-\right]_2 -C\overset{CH_3}{\underset{CH_3}{\diagdown}}$$

l)
$$ClCH_2CH_2O-\underset{\underset{n-C_6H_{13}O}{|}}{\overset{\overset{O}{\|}}{P}}-O-\underset{}{\underset{}{\bigcirc}}-O-\underset{\underset{O-n-C_6H_{13}}{|}}{\overset{\overset{O}{\|}}{P}}-OCH_2CH_2Cl$$

m)
$$ClCH_2CH_2O-\underset{\underset{\underset{C_2H_5}{|}}{C_4H_9CHCH_2O}}{\overset{\overset{O}{\|}}{P}}-O-\underset{}{\underset{}{\bigcirc}}-O-\underset{\underset{\underset{C_2H_5}{|}}{OCH_2CHC_4H_9}}{\overset{\overset{O}{\|}}{P}}-OCH_2CH_2Cl$$

The plasticizers of the present invention are highly viscous, colorless and undistillable liquids.

The process for making the flame-retardant plasticizers of general formula (I)

$$ClCH_2CH_2O-\underset{\underset{OR_1}{|}}{\overset{\overset{O}{\|}}{P}}-ORO-\underset{\underset{OR_1}{|}}{\overset{\overset{O}{\|}}{P}}-OCH_2CH_2Cl \quad (I)$$

in which R stands for an alkylene radical having from 2 to 6 carbon atoms and being halogen-substituted, if desired, a —CH₂CH₂—O—CH₂CH₂—radical, a phenylene or an alkyl or halogenoalkyl-substituted diphenylenemethane radical and R₁ stands for a branched or unbranched alkyl radical having from 6 to 18 carbon atoms, comprises:

a. reacting a compound of general formula (II)

$$ClCH_2CH_2O-\underset{\underset{H}{|}}{\overset{\overset{O}{\|}}{P}}-ORO-\underset{\underset{H}{|}}{\overset{\overset{O}{\|}}{P}}-OCH_2CH_2Cl \quad (II)$$

in which R has the meaning given above, with at least stoichiometric proportions of chlorine gas at temperatures within the range about 0° and 5° C in the presence of a solvent being difficultly soluble for hydrogen chloride to give a compound of general formula (III)

$$ClCH_2CH_2O-\underset{\underset{Cl}{|}}{\overset{\overset{O}{\|}}{P}}-ORO-\underset{\underset{Cl}{|}}{\overset{\overset{O}{\|}}{P}}-OCH_2CH_2Cl \quad (III)$$

in which R has the meaning given above, terminating the reaction and freeing the reaction solution from chlorine gas in excess or resulting hydrogen chloride by introducing an inert gas thereinto, b. effecting the formation of the formula (I) compound by admixing the reaction solution from stage (a) at temperatures within the range about 15° and 50° C and while introducing further inert gas thereinto with a stoichiometric proportion of an alcohol of general formula (IV)

$$R_1OH \quad (IV),$$

in which R₁ stands for a branched or unbranched alkyl radical having from 6 to 18 carbon atoms, terminating the reaction and distilling off the solvent, and c. freeing the crude product of general formula (I) from stage (b) from adhering hydrogen chloride by reacting the hydrogen chloride with at least stoichiometric proportions of ethylene oxide at a temperature within the range about 60° and 120° C, and purifying the crude product by distilling off ethylene chlorohydrin and ethylene oxide in excess.

The plasticizers of the present invention are more preferably made using compounds of the general formula (I), in which the substituent R stands for an ethylene, hexamethylene or diethyleneglycol radical or one of the following two radicals $$-CH_2-\underset{\underset{CH_2Br}{|}}{\overset{\overset{CH_2Br}{|}}{C}}-CH_2- \qquad -\underset{}{\underset{}{\bigcirc}}-\underset{\underset{CH_3}{|}}{\overset{\overset{CH_3}{|}}{C}}-\underset{}{\underset{}{\bigcirc}}-$$

and R₁ stands for an n-hexyl, 2-ethylhexyl- dodecyl or stearyl radical. In those cases in which the substituent R stands for a halogenoalkyl-substituted diphenylenemethane radical, it is preferable for chlorine or bromine to be used as the halogen substituents.

The starting material used in stage (a) should conveniently be chlorinated in the presence of methylene chloride, dichloroethane or petroleum ether as a solvent. Hydrogen chloride which originates from this reaction may be expelled from the reaction mixture, for example, by the introduction of nitrogen so that the resulting intermediary product is substantially free from hydrogen halide.

The esterification of the above intermediary product in stage (b) may be effected at preferred temperatures within the range 40° and 50° C with the use, for example, of n-hexanol, 2-ethylhexanol, dodecanol or stearyl alcohol.

The crude product obtained in stage (b) should preferably be freed from hydrogen chloride with the aid of ethylene oxide at preferred temperatures within the range 80° and 120° C and in the presence of about 0.1–0.2 weight % of a disodium phosphate regulator, based on the quantity of the product of general formula (I). With respect to ethylene oxide, it is preferable for it to be used in proportions within the range 0.1 and 0.5 mol, for example, per mol of the product of general formula (I).

The general formula (II) compound used as starting material in processing stage (b) is known and can be made by the process described in U.S. Pat. No. 3,147,299, Examples 1 and 2.

The flame-retardant plasticizers are incorporated with PVC in the usual manner, i.e., by intimately mixing together the individual components, e.g., in an intense mixer, and plasticizing the resulting mixture on a suitable roller at increased temperature so as to obtain PVC-sheets having a certain thickness. Between about 0.5 and 70 weight %, preferably 1 and 20 weight %, of plasticizer is generally incorporated into PVC.

The flame-retardant PVC-plasticizers compare very favorably with customary plasticizers in enabling improved flame-retardant properties not obtainable heretofore to be imparted to PVC substantially without any adverse affects on its other properties.

The following Examples illustrate the invention which is, however, not limited thereto.

EXAMPLE 1

A plasticizer of the following formula was made

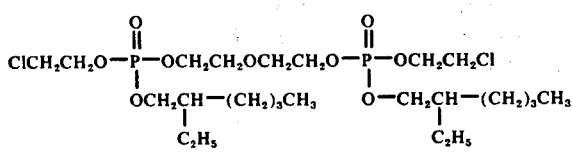

To this end, a solution of 1373.4 g of $PCl_3$ (10.0 mol) and 3.0 l of methylene chloride was introduced into a reactor provided with reflux condenser and agitator and 620.7 g of ethyleneglycol (10.0 mol) was added dropwise with agitation at room temperature. The reaction was complete after about 1 hour. After that time, a further 5.0 mol of diethyleneglycol was added to the reaction mixture so that the reaction temperature remained within the limits of 20°–25° C. Following this, chlorine was introduced at 0°–5° C into the solution obtained until the solution assumed a yellow-green coloration which indicated the end of the reaction. Chlorine gas in excess and resulting chlorohydrocarbon were expelled by means of nitrogen. The introduction of nitrogen was continued and 651 g (5.0 mol) of 2-ethylhexanol was added at room temperature. After all had been added, the temperature was increased for a period of about 1 hour to 40° C, the solution was distillatively freed from the solvent and a highly viscous colorless liquid was obtained as the residue. It was admixed at 90° C first with 1 g of $Na_2HPO_4$ and then with ethylene oxide until continuous reflux after about 15–30 minutes indicated that ethylene oxide ceased to be absorbed. 1.5 mol of ethylene oxide underwent reaction. Ethylene oxide in excess and resulting ethylene-chlorohydrin were distilled off under vacuum. The distillation residue was the phosphoric acid ester having the formula indicated above. It had an acid number of less than 1 mg of KOH/g substance and was obtained in a yield of 97% of the theoretical.

The ester was analyzed and the following results were obtained:

| Found: | Calculated: |
|---|---|
| P 9.9 % | 10.5 % |
| Cl 12.3 % | 12.2 % |

EXAMPLE 2

A plasticizer of the following formula was made

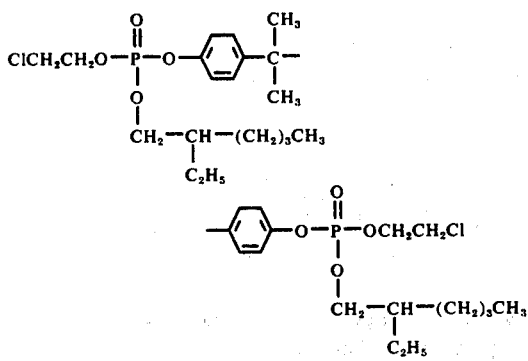

To this end, a solution of 274.7 g of $PCl_3$ (2.0 mol) and 1.0 l of methylene chloride was introduced into a reactor provided with reflux condenser and agitator and 124 g of ethyleneglycol (2.0 mol) was added dropwise with agitation at room temperature. The reaction was complete after about 1 hour. After that time, a further 1.0 mol of p,p'-isopropylidene diphenol was added to the reaction mixture so that the reaction temperature remained within the limits of 20°–25° C. Following this, chlorine was introduced at 0°–5° C into the solution obtained until the solution assumed a yellow-green coloration which indicated the end of the reaction. Chlorine gas in excess and resulting chlorohydrocarbon were expelled from the solution by means of nitrogen. The introduction of nitrogen was continued and 260 g (2.0 mol) of 2-ethylhexanol was added at room temperature. After all had been added, the temperature was increased for a period of about 1 hour to 40° C, the solution was distillatively freed from the solvent and a highly viscous colorless liquid was obtained as the residue. It was admixed at 90° C first with 1 g of $Na_2HPO_4$ and then with ethylene oxide until continuous reflux after about 15–30 minutes indicated that ethylene oxide ceased to be absorbed. 0.25 mol of ethylene oxide underwent reaction. Ethylene oxide in excess and resulting ethylene-chlorohydrin were distilled off under vacuum. The distillation residue was the phosphoric acid ester having the formula indicated above. It had an acid number of less than 1 mg of KOH/g substance and was obtained in a yield of 98% of the theoretical.

The ester was analyzed and the following results were obtained:

| Found: | Calculated: |
|---|---|
| P 8.7 % | 8.4 % |
| Cl 9.9 % | 9.6 % |

EXAMPLE 3

The products of the present invention were tested as to their flame-retardant efficiency in polyvinyl chloride, their influence on the notched impact strength of polyvinyl chloride and their influence on the migration of the plasticizer in the plastics. To this end, various polyvinyl chloride specimens, identified as specimens A–E were prepared. Specimen A was free from flame-retardant agent, specimens B and C each contained a known flame-retardant agent and specimens D and E each contained a flame-retardant agent made in accordance with the present invention.

Specimens B–E having the flame-retardant agents incorporated therein were composed as follows (in parts by weight):

70 parts of suspension-made polyvinyl chloride having a K-value of 70,
1.05 part of a blend of 75 weight % of di-n-octyl tin mercaptide and 25 weight % of glycerol mono fatty acid ester,
0.105 part of p,p'-isopropylidene diphenol,
22.5 parts of dioctyl phthalate,
2.5 parts of epoxidized soybean oil, and 5.0 parts of flame-retardant agent As regards composition, specimen A differed from specimens B–E by the fact that it was free from flame-retardant agent but contained 27.0 parts by weight of dioctyl-phthalate and 3.0 parts by weight of epoxidized soybean oil.

The individual powder blends were plasticized on a roller for 10 minutes at 160° C and made into sheets having the thickness necessary for the tests described hereinafter.

The plasticizer migration in specimens A–E was tested as described in DIN test (German Industrial Standard) No. 59 407, process A. To this end, the specimens were made into round moulded plates 1 mm thick and 50 mm in diameter which were embedded in active carbon and stored for 24 hours at 100° C. After further storage for 24 hours at room temperature, the loss in weight in %, of the individual plates was determined.

The flexibility and freeze resistance of the specimens were identified by determining the notched impact strength at 0 and −10° C, respectively, in accordance with DIN test (German Industrial Standard) 53 453. High notched impact strength values mean high flexibility.

The burn-up behaviour of the specimens was determined by the small burner test described in DIN test (German Industrial Standard) 53 438, which permitted the specimens to be categorized (burning classes K1, K2 or K3) and the individual burning classes to be further identified by burning time and burn-up length.

The test results obtained are indicated in the following Table II:

Table

| Specimen | I | II | III | IV | V | VI |
|---|---|---|---|---|---|---|
| A | 3.3 | 6.1 | 2.7 | K3/0.2 mm | — | — |
| B | 2.1 | 3.3 | 1.9 | K3/0.2 mm | — | — |
| C | 3.0 | 4.0 | 2.9 | K1/0.2 mm | 48 | 140 |
| D | 2.2 | 9.3 | 2.9 | K1/0.2 mm | 1 | 60 |
| E | 2.1 | 3.1 | 1.9 | K1/0.2 mm | 1 | 61 |

In the above Table, the following symbols have the following meanings:
A: Polyvinyl chloride free from flame-retardant agent
B: Polyvinyl chloride containing tricresyl phosphate
C: Polyvinyl chloride containing liquid chlorinated paraffin (chloroparaffin) with 56 weight % of chlorine therein
D: Polyvinyl chloride containing the product of Example 1
E: Polyvinyl chloride containing the product of Example 2
Column I: Migration of plasticizer (DIN-test 53 407), loss in weight in %
Column II: Notched impact strength (DIN-test 53 453) identified at 0° C in kg.cm/cm²
Column III: Notched impact strength (DIN-test 53 453) identified at −10° C in kg.cm/cm²
Column IV: Burning class, sheet specimens 0.2 mm thick
Column V: Burning period in seconds
Column VI: Burn-up length in mm The results indicated in the above Table show that polyvinyl chloride specimens D and E having the flame-retardant agents of the present invention incorporated therein compare favorably with comparative specimens B and C, and that the initial properties of the specimens remain unaffected by the addition of the products of the present invention.

We claim:

1. A flame-retardant composition consisting essentially of polyvinyl chloride and a plasticizer therefor of the formula

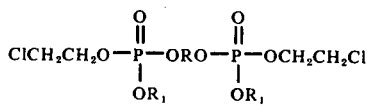

in which R stands for an alkylene radical or a halogen-substituted alkylene radical having from 2 to 6 carbon atoms, a —CH$_2$CH$_2$—O—CH$_2$CH$_2$—radical, a phenylene or an alkyl or halogenoalkyl-substituted diphenylenemethane radical, and R$_1$ stands for a branched or unbranched alkyl radical having from 6 to 18 carbon atoms.

2. Composition as claimed in claim 1, wherein the substituent R stands for an ethylene, hexa-methylene or diethylene-glycol radical or for one of the following two radicals

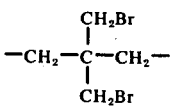 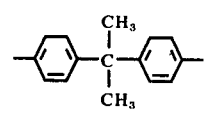

3. Composition as claimed in claim 1, wherein the substituent R$_1$ stands for a n-hexyl, 2-ethylhexyl, dodecyl or stearyl radical.

4. Composition as claimed in claim 1, wherein the halogen attached to the halogeno-substituted diphenylene methane radical is chlorine or bromine.

5. The composition as claimed in claim 1, wherein the plasticizer has the formula:

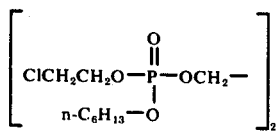

6. The composition as claimed in claim 1, wherein the plasticizer has the formula:

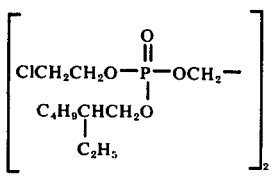

7. The composition as claimed in claim 1, wherein the plasticizer has the formula:

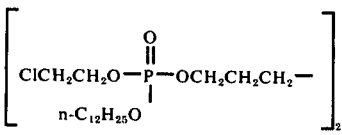

8. The composition as claimed in claim 1, wherein the plasticizer has the formula:

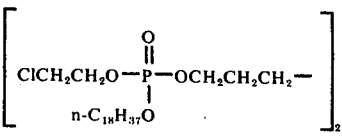

9. The composition as claimed in claim 1, wherein the plasticizer has the formula:

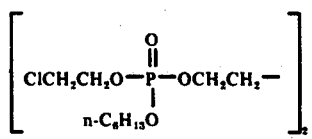

10. The composition as claimed in claim 1, wherein the plasticizer has the formula:

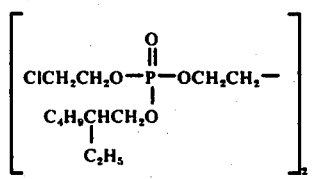

11. The composition as claimed in claim 1, wherein the plasticizer has the formula:

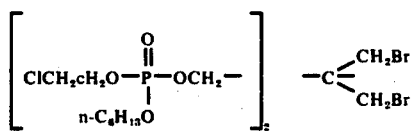

12. The composition as claimed in claim 1, wherein the plasticizer has the formula:

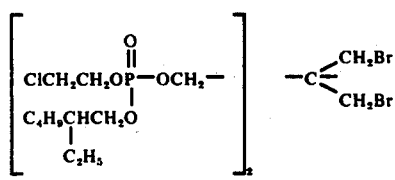

13. The composition as claimed in claim 1, wherein the plasticizer has the formula:

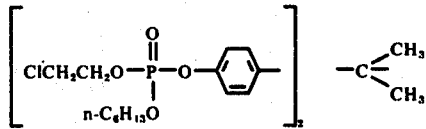

14. The composition as claimed in claim 1, wherein the plasticizer has the formula:

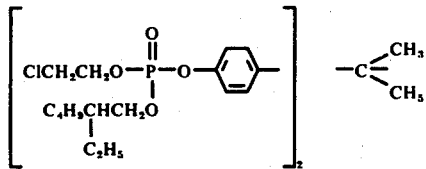

15. The composition as claimed in claim 1, wherein the plasticizer has the formula:

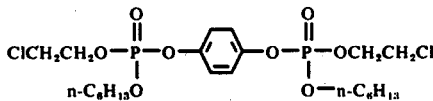

16. The composition as claimed in claim 1, wherein the plasticizer has the formula:

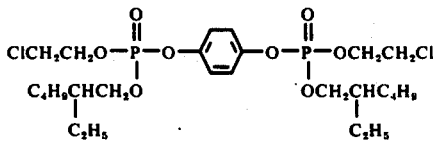

17. The composition as claimed in claim 1, wherein the amount of the plasticizer is about 0.5 – 70% by weight of the polyvinyl chloride. j

18. The composition as claimed in claim 1, wherein the amount of the plasticizer is 1 – 20% by weight of the polyvinyl chloride.

* * * * *